United States Patent
Hurley

(10) Patent No.: US 9,412,023 B1
(45) Date of Patent: Aug. 9, 2016

(54) METHOD TO DETERMINE WETTABILITY OF ROCK SAMPLES USING IMAGE ANALYSIS

(71) Applicant: Neil Francis Hurley, Houston, TX (US)

(72) Inventor: Neil Francis Hurley, Houston, TX (US)

(73) Assignee: CHEVRON U.S.A. INC., San Ramon, CA (US)

( * ) Notice: Subject to any disclaimer, the term of this patent is extended or adjusted under 35 U.S.C. 154(b) by 23 days.

(21) Appl. No.: 14/673,930

(22) Filed: Mar. 31, 2015

(51) Int. Cl.
*G06K 9/00* (2006.01)
*E21B 49/00* (2006.01)
*G06T 7/00* (2006.01)
*G01N 1/04* (2006.01)

(52) U.S. Cl.
CPC ............. *G06K 9/0063* (2013.01); *E21B 49/00* (2013.01); *G01N 1/04* (2013.01); *G06T 7/0079* (2013.01)

(58) Field of Classification Search
None
See application file for complete search history.

(56) References Cited

U.S. PATENT DOCUMENTS

| | | | | |
|---|---|---|---|---|
| 8,676,556 | B2* | 3/2014 | Deffenbaugh et al. | G01V 11/00 703/10 |
| 9,140,117 | B2* | 9/2015 | De Prisco | G06T 17/05 |
| 2011/0181701 | A1* | 7/2011 | Varslot et al. | G06T 7/0024 348/46 |
| 2015/0355158 | A1* | 12/2015 | Lander et al. | G01N 33/24 702/2 |

OTHER PUBLICATIONS

Al-Raoush, "Impact of Wettability on Pore-Scale Characteristics of Residual Nonaqueous Phase Liquids," Environ. Sci. Technol. 2009, 43, 4796-4801.*

Abdallah, W., et al.; "Fundamentals of Wettability"; Oilfield Review, 2007, pp. 44-61 (with attached drawings).
Anderson, W.G.; Wettability Literature Survey—Part 1: Rock/Oil/Brine Interactions and the Effects of Core Handling on Wettability: Journal of Petroleum Technology, Oct. 1986, vol. 38, pp. 1125-1144; SPE 13932-PA.
Anderson, W.G.; Wettability Literature Survey—Part 2: Wettability Measurement: Journal of Petroleum Technology, Nov. 1986, vol. 38, pp. 1246-1262; SPE 13933-PA.
Anderson, W.G.; Wettability Literature Survey—Part 3: The Effects of Wettability on the Electrical Properties of Porous Media: Journal of Petroleum Technology, Dec. 1986, vol. 38, pp. 1371-1378; SPE 13934-PA.
Anderson, W.G.; Wettability Literature Survey—Part 4: Effects of Wettability on Capillary Pressure: Journal of Petroleum Technology, Oct. 1987, vol. 39, pp. 1283-1300; SPE 15271-PA.
Anderson, W.G.; Wettability Literature Survey—Part 5: The Effects of Wettability on Relative Permeability: Journal of Petroleum Technology, Nov. 1987, vol. 39, pp. 1453-1468; SPE 16323-PA.
Anderson, W.G.; Wettability Literature Survey—Part 6: The Effects of Wettability on Waterflooding: Journal of Petroleum Technology, Dec. 1987, vol. 39, pp. 1605-1622; SPE 16471-PA.

* cited by examiner

*Primary Examiner* — Vu Le
*Assistant Examiner* — Alexander J Lesnick
(74) *Attorney, Agent, or Firm* — Albert K. Shung; Marie L. Clapp

(57) ABSTRACT

A method is disclosed for determining wettability in a subsurface reservoir. Embodiments of the method utilize image analysis techniques for determining wettability indicator values. Wettability indicator values may be determined based on a hydrocarbon wet fraction and a water wet fraction of pore linings, which may both be determined by image analysis of pore walls lined with hydrocarbons using images of sections obtained from core samples. Further details and advantages of various embodiments of the method are described in more detail herein.

9 Claims, 8 Drawing Sheets

METHOD TO DETERMINE WETTABILITY OF ROCK SAMPLES USING IMAGE ANALYSIS

CROSS-REFERENCE TO RELATED APPLICATIONS

Not applicable.

STATEMENT REGARDING FEDERALLY SPONSORED RESEARCH OR DEVELOPMENT

Not applicable

BACKGROUND

1. Field of the Invention

This invention relates generally to the field of geological exploration for hydrocarbons. More specifically, the invention relates to a method of determining wettability of rock samples.

2. Background of the Invention

Wettability is a property of rocks which measures the preference of a fluid such as oil, gas, or water, to be in contact with the surface of a rock pore. The pore surface may be a mineral or a mineral which is partially or completely coated with a hydrocarbon material and/or "heavy organic materials." For the purposes of this disclosure, these "heavy organic materials" are highly viscous and/or semi-solid hydrocarbon materials. Examples of heavy organic materials include, for example and without limitation, bitumen, resins, asphaltenes, and pyrobitumen. Bitumen is organic matter soluble in organic solvents, such as carbon bisulfide. Asphaltene is organic matter that is insoluble in straight-chain solvents, such as pentane or heptane. Resin molecules are aromatic ring hydrocarbons. Pyrobitumen is insoluble, thermally altered bitumen or oil. To be clear, as used herein, heavy organic materials are to be distinguished from lighter, less viscous hydrocarbon crude oil components such as alkanes, naphtalenes, aromatics, etc. As used herein, these lighter, less viscous or lighter hydrocarbon crude oil components will be referred generically as "light hydrocarbon materials." Typically, for rock or core samples obtained from a reservoir, wettability is determined for a very small number of samples. Limited results are generally extrapolated to large volumes of rocks. Wettability is a parameter which has an impact on a number of reservoir project economics. For example, wettability influences oil recovery from a reservoir. Additionally, wettability has an effect on waterflood and gasflood performance.

Consequently, there is a need for improved methods and systems to determine wettability of rock samples from a reservoir.

BRIEF SUMMARY

A method is disclosed for determining wettability of rock samples from image analysis. Embodiments of the method utilize image analysis techniques for determining a parameter known as a wettability indicator (WI). The wettability indicator may be determined based on a hydrocarbon wet fraction and a water wet fraction of pore linings, which may both be determined by image analysis of sample sections. Further details and advantages of various embodiments of the method are described in more detail herein.

In an embodiment, a computer-implemented method of determining wettability in a subsurface reservoir comprises (a) acquiring one or more core samples from the subsurface reservoir. The method also comprises (b) preparing a plurality of sections from the core samples for image analysis. In addition, the method comprises (c) obtaining a plurality of digital images from each section from a digital imaging device. The method further comprises (d) segmenting each digital image into at least a hydrocarbon phase, a water bearing pore phase, and a rock phase. Moreover, the method comprises (e) determining a wettability indicator based on a hydrocarbon wet fraction and a water wet fraction, wherein the hydrocarbon wet fraction and the water wet fraction are determined based on the segmenting in (d), and wherein at least one of (c) through (e) is performed on a computer.

In another embodiment, a system comprises an imaging device for obtaining one or more digital images of a plurality of imaging sections from one or more core samples from a subsurface reservoir. The system also comprises an interface for receiving one or more user inputs. The system also comprises a memory resource, the memory resource configured to store the digital images. The system further comprises input and output functions for presenting and receiving communication signals to and from a human user. In addition, the system comprises one or more central processing units for executing program instructions and program memory, coupled to the central processing unit, for storing a computer program including program instructions that, when executed by the one or more central processing units, cause the computer system to perform a plurality of operations for determining wettability of a subsurface reservoir, the plurality of operations comprising (a) segmenting each digital image into at least a hydrocarbon phase, a water bearing pore phase, and a rock phase. Moreover, the operations comprise (b) determining a wettability indicator based on a hydrocarbon wet fraction and a water wet fraction, wherein the hydrocarbon wet fraction and the water wet fraction are determined based on the segmenting in (a).

The foregoing has outlined rather broadly the features and technical advantages of the invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other structures for carrying out the same purposes of the invention. It should also be realized by those skilled in the art that such equivalent constructions do not depart from the spirit and scope of the invention as set forth in the appended claims.

BRIEF DESCRIPTION OF THE DRAWINGS

For a detailed description of the preferred embodiments of the invention, reference will now be made to the accompanying drawings in which.

NOTATION AND NOMENCLATURE

Certain terms are used throughout the following description and claims to refer to particular system components. This document does not intend to distinguish between components that differ in name but not function.

In the following discussion and in the claims, the terms "including" and "comprising" are used in an open-ended fashion, and thus should be interpreted to mean "including, but not limited to . . . ". Also, the term "couple" or "couples" is intended to mean either an indirect or direct connection. Thus, if a first device couples to a second device, that connection may be through a direct connection, or through an indirect connection via other devices and connections.

DETAILED DESCRIPTION OF THE PREFERRED EMBODIMENTS

Referring now to the Figures, embodiments of the disclosed methods will be described. As a threshold matter, embodiments of the methods may be implemented in numerous ways, as will be described in more detail below, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the disclosed methods are discussed below. The appended drawings illustrate only typical embodiments of the disclosed methods and therefore are not to be considered limiting of its scope and breadth.

Figure 3:
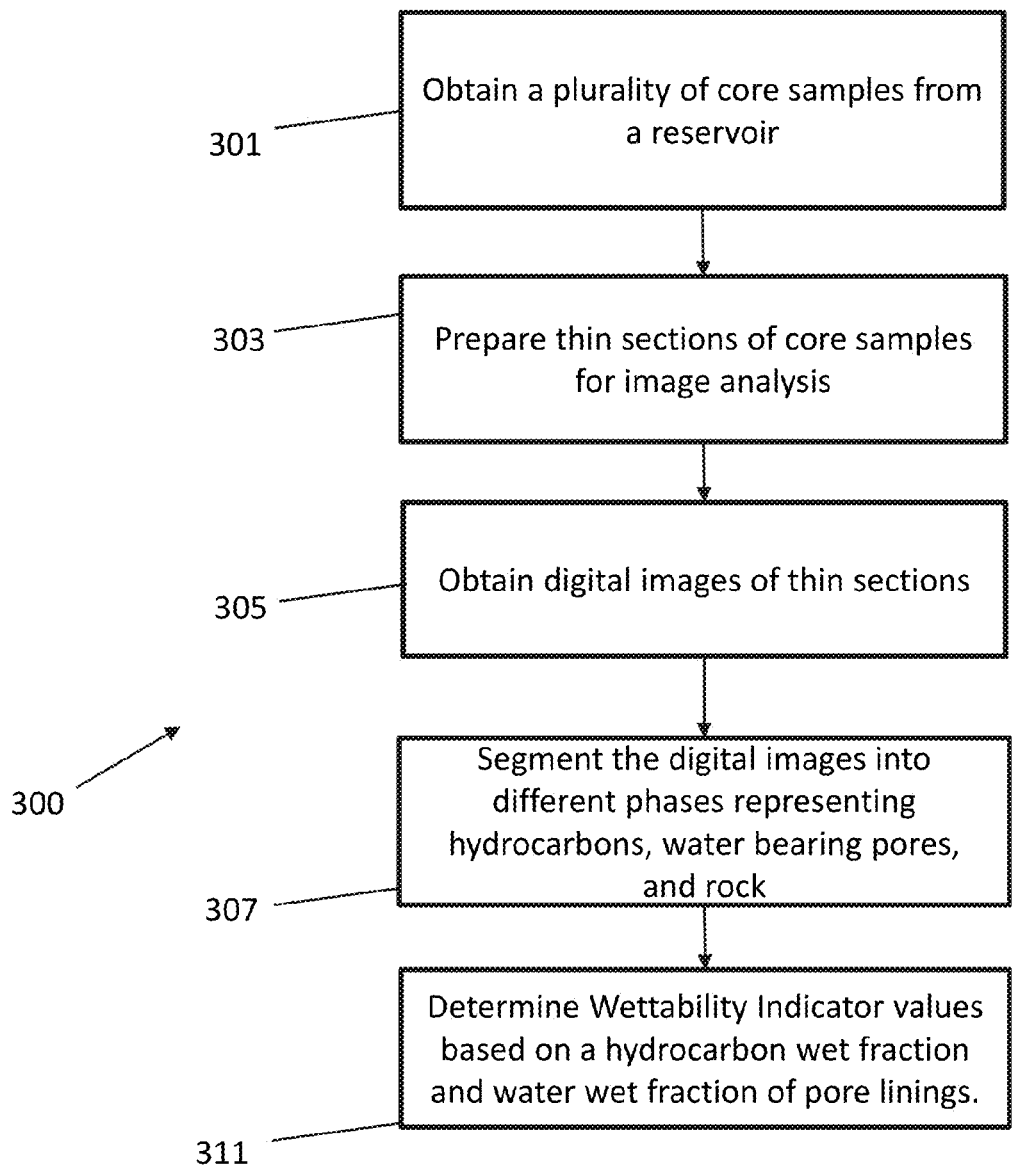
FIG. 3 illustrates a flowchart of an embodiment of the method.

In an embodiment, referring to FIG. 3, the method 300 involves obtaining or acquiring one or more core samples which are representative of a reservoir of interest in block 301. The core samples may be acquired using any method known to those of skill in the art. Thin slices or sections may then be prepared for image analysis in 303. The thin sections from the core samples may be prepared via any methods known to those of skill in the art. The sections may be imaged or viewed through any methods known to those of skill in the art in 305. In particular, images of the core sample sections may be captured using a confocal laser microscope. Other imaging techniques may be used without limitation, including micro-CT (micro computed tomography), scanning electron microscopy, reflected light microscopy, fluorescent microscopy and the like. These images may be stored on a computer for later analysis.

Figure 1A:
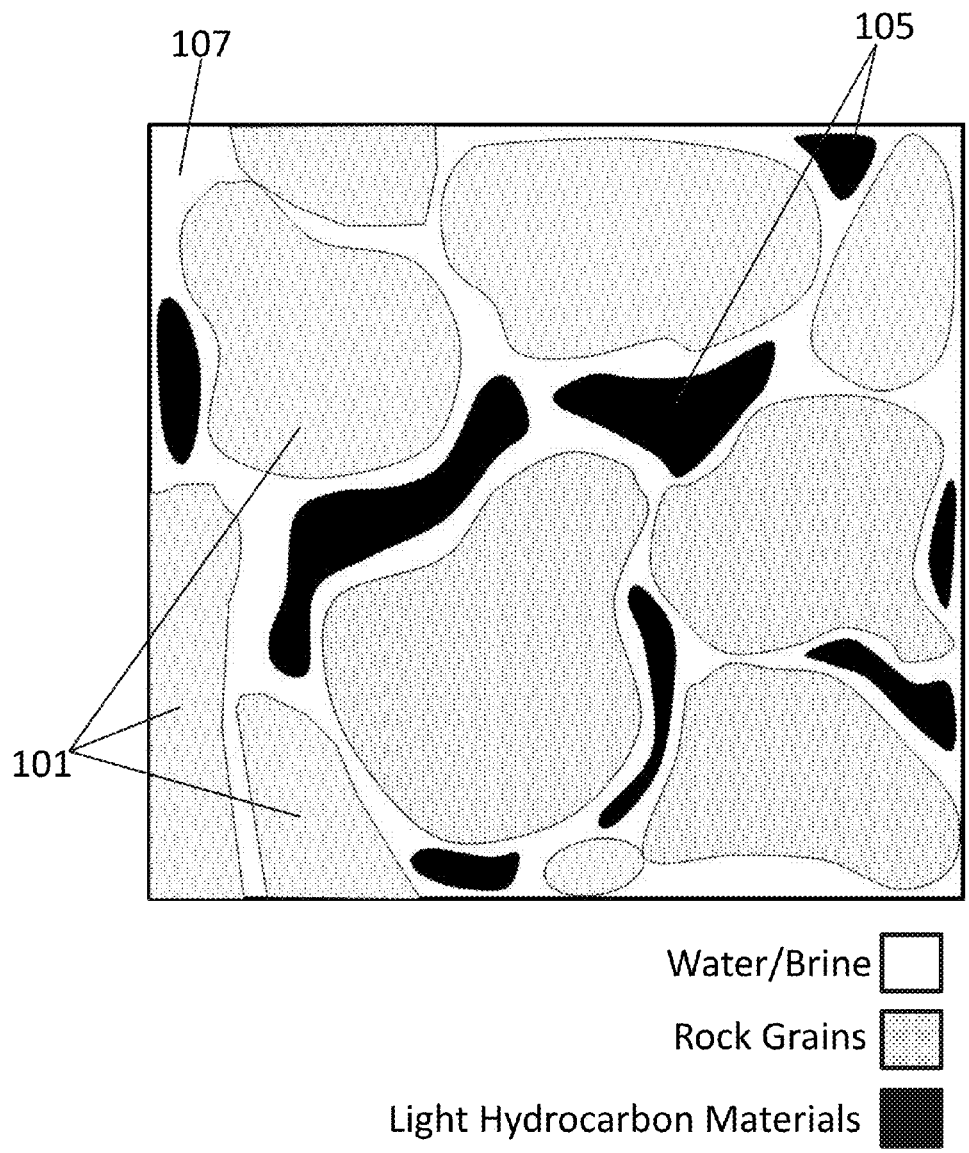
FIG. 1A illustrates a simulation of an exemplary thin image section from a water wet reservoir.
Figure 1B:
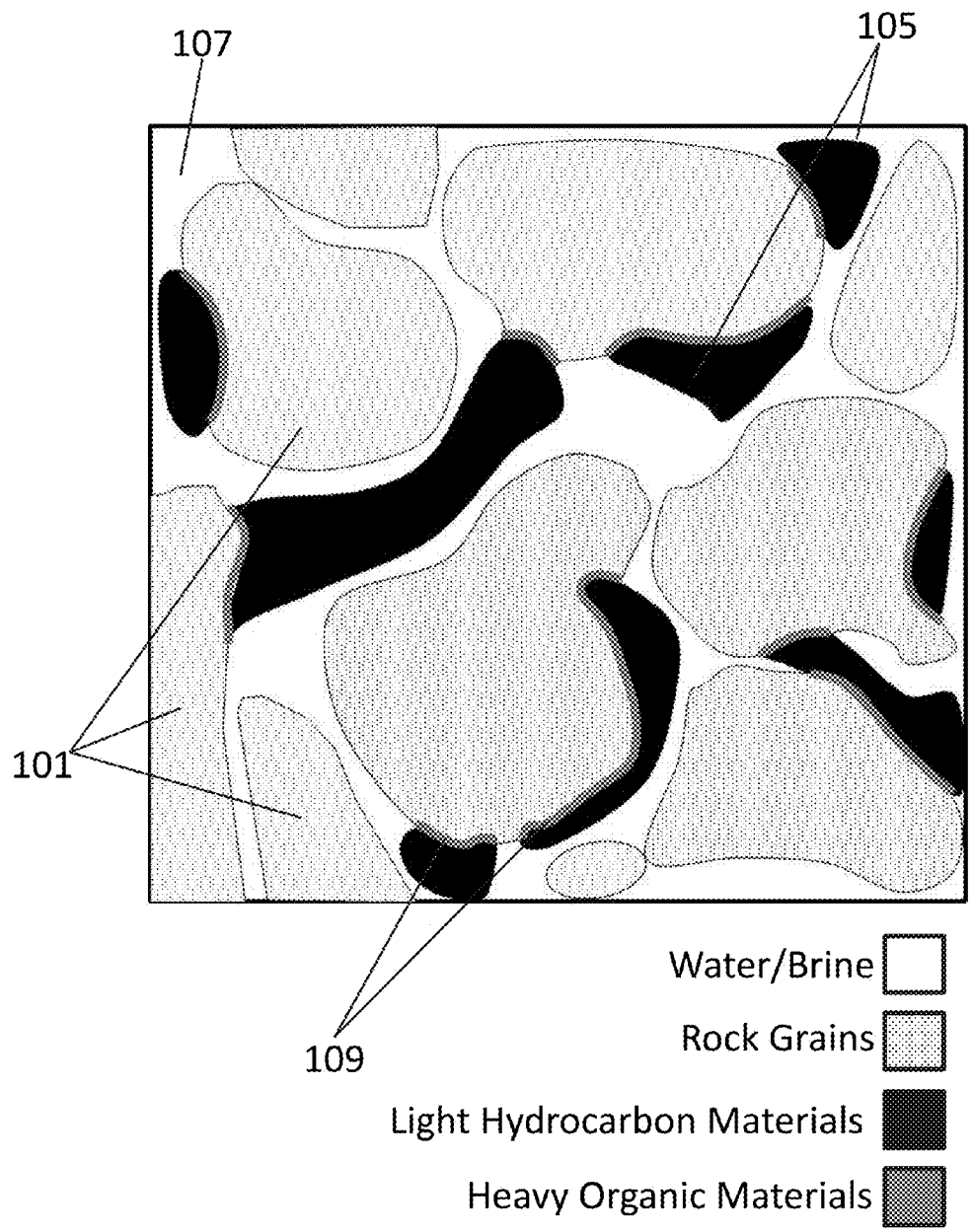
FIG. 1B illustrates a simulation of an exemplary thin image section from a mixed wet reservoir.
Figure 1C:
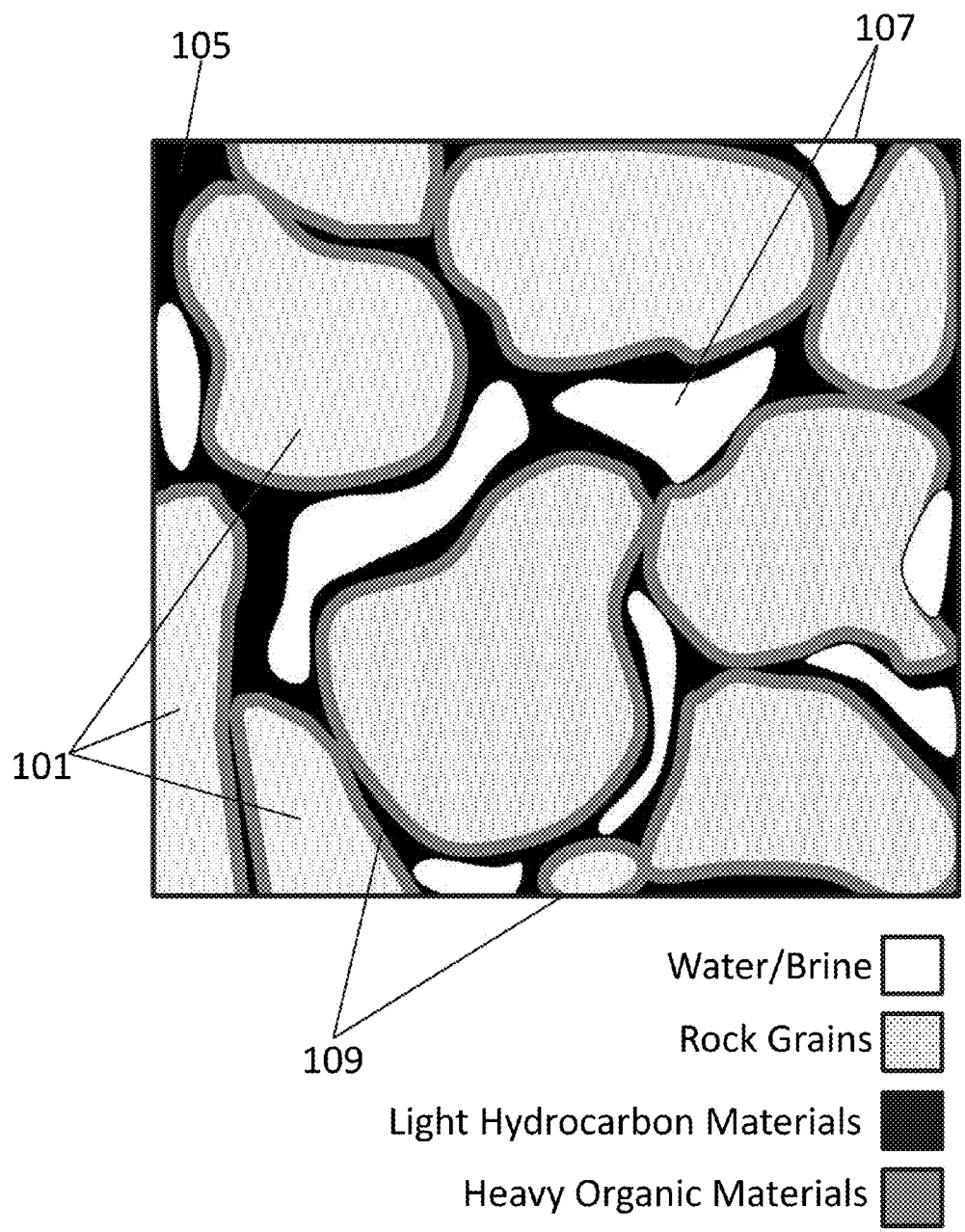
FIG. 1C illustrates a simulation of an exemplary thin image section from a hydrocarbon wet reservoir.

Once the images of the sections have been obtained or acquired, the images may be segmented into areas of water bearing pores, mineral or rock, and hydrocarbon 307. For purposes of this disclosure, a water bearing pore is a pore which contains water and/or brine. As is known in the art, image segmentation is the process of partitioning a digital image into multiple segments (or sets of pixels). Image segmentation is typically used to locate objects and boundaries (lines, curves, etc.) in images. In this application, segmentation is used to locate the boundaries of rock, hydrocarbons and pores filled with water/brine. More precisely, image segmentation is the process of assigning a label to every pixel in an image such that pixels with the same label share certain characteristics. Software, such as NIH (National Institute of Health) ImageJ, may be used to segment the images without limitation. Any techniques and/or algorithms known to those of skill in the art may be used for image segmentation including without limitation, edge detection, thresholding, clustering, or combinations thereof. FIGS. 1A-1C show schematically simulated images of thin sections that have been segmented into the various phases of rock grains 101, pores filled with brine or water 107, light hydrocarbon materials 105 and heavy organic materials 109. In reservoirs where heavy organic materials are present, it may be assumed that any surface coated with heavy organic matter or material and/or light hydrocarbon material is considered oil wet, and any uncoated mineral or rock phase is water wet. It is also assumed that the light hydrocarbon materials and heavy organic materials are visible using some form of microscopy, and these heavy organic or light hydrocarbon coatings were not removed by solvents or cleaning agents before or during thin section preparation.

In 311 of method 300, once segmented into phases, a fraction or ratio of the total perimeter of hydrocarbon lined pores (i.e. pores lined with heavy organic materials and/or light hydrocarbon materials) versus the total perimeter of pores (total pore length) may be determined, which may be expressed as:

$$\frac{\sum \text{length of hydrocarbon lined pores}}{\sum \text{total perimeter of pores}} = \text{hydrocarbon wet fraction}$$

This fraction may be referred to as the hydrocarbon wet fraction for purposes of this disclosure. The fraction of perimeter of pores unlined with light hydrocarbons and/or heavy organic materials (i.e. water or rock) (pore length of water lined pores) versus the total perimeter of pores (total pore length) may also be determined, which may be expressed as:

$$\frac{\sum \text{length of unlined pores}}{\sum \text{total perimeter of pores}} = \text{water wet fraction}$$

The determined fraction of perimeter of pores unlined with heavy organic materials or light hydrocarbons (i.e. water or rock) versus the total perimeter of pores may be referred to as the water wet fraction. For the purposes of this invention, this fraction is also known as the wettability indicator. Values range from 0 (hydrocarbon wet) to 1 (water wet).

Figure 2A:
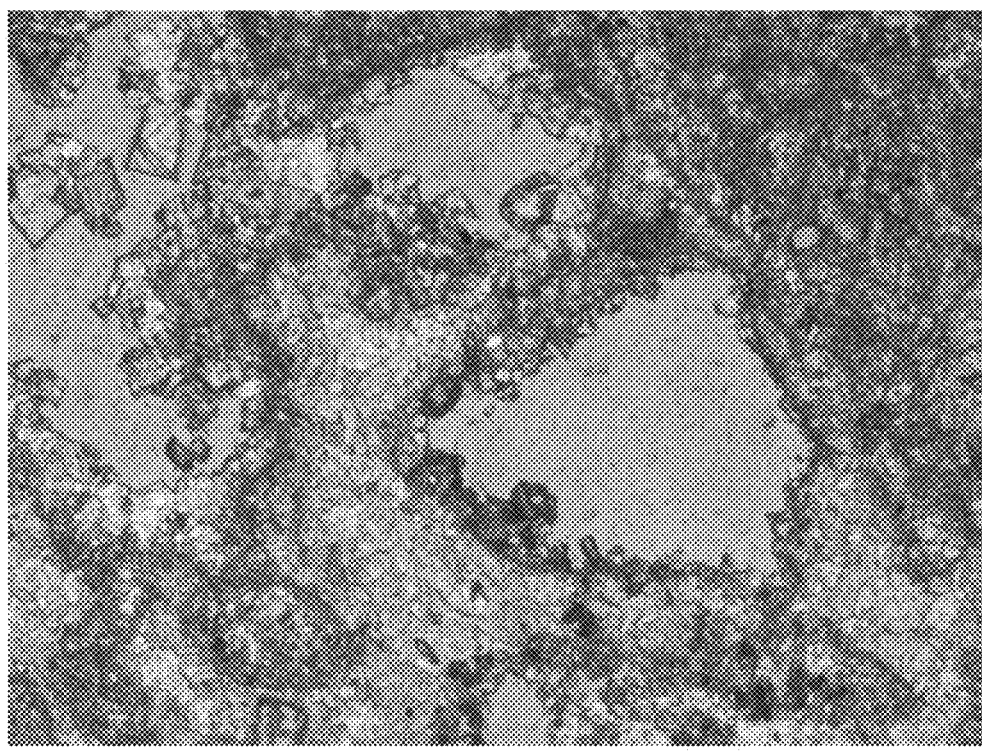
FIG. 2A illustrates an actual exemplary thin image section from a water wet reservoir.

This calculated or determined wettability indicator may be then be used to assess hydrocarbon wettability of the reservoir. That is, for example, a higher value of the wettability indicator may indicate the reservoir has increased water wettability. FIGS. 1A-1C and FIGS. 2A-2C illustrate examples of the different types of reservoirs that may be encountered. These examples are shown for exemplary purposes only. Any type of reservoir may be analyzed with the disclosed methods. FIG. 1A shows an example of a water wet reservoir. The rock grains 101 are wetted only by water/brine 107. As such, the hydrocarbon wet fraction would be 0 whereas the water wet fraction would be 1. The wettability indicator would also be equal to 1. Accordingly, this would be an example of non-hydrocarbon wet reservoir sample. FIG. 2A shows an example from an actual thin section obtained from a reservoir.

Figure 2B:
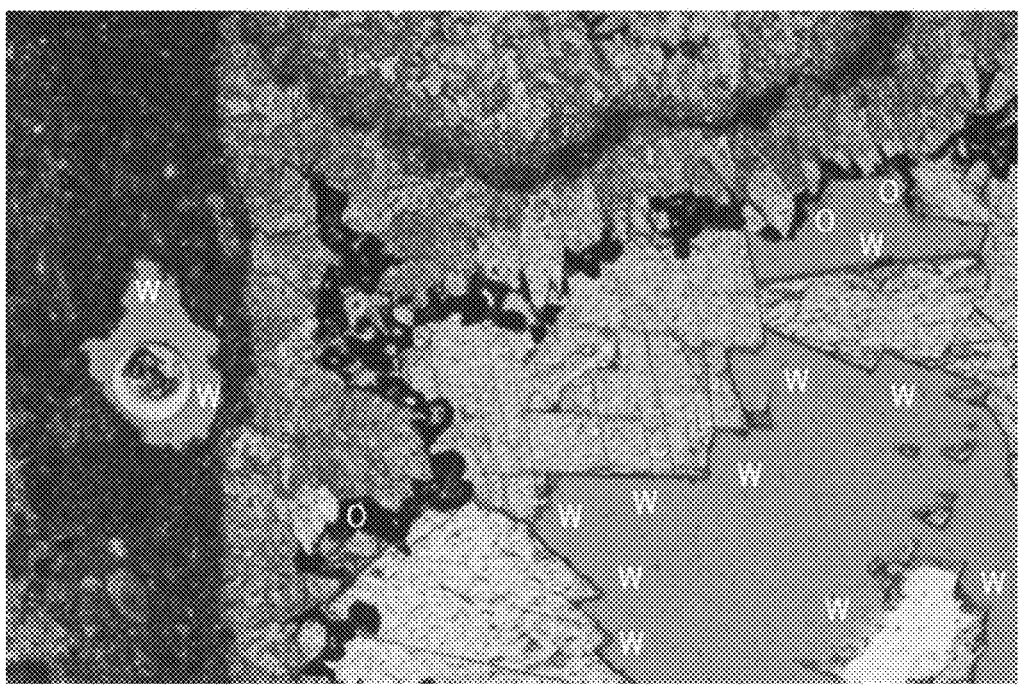
FIG. 2B illustrates an actual exemplary thin image section from a mixed wet reservoir; W represents interpreted water-wet portions of the pore lining; O represents interpreted oil-wet portions of the pore lining.

FIG. 1B shows an example of a mixed hydrocarbon wet reservoir. The rock grains 101 are a mix between those wetted by hydrocarbons 105 and those wetted by water 107. In addition, there are heavy organic material coatings 109, indicated by gray lines, between the light hydrocarbons and some parts of rock grains. In embodiments, heavy organic material coatings would be considered hydrocarbon wet. As such, in this particular example, the hydrocarbon wet fraction may be 0.25 whereas the water wet fraction would be 0.75. The wettability indicator would be equal to 0.75. Accordingly, this would be an example of a mixed hydrocarbon and water wet reservoir sample. FIG. 2B shows an example from an actual thin section obtained from a reservoir.

Figure 2C:
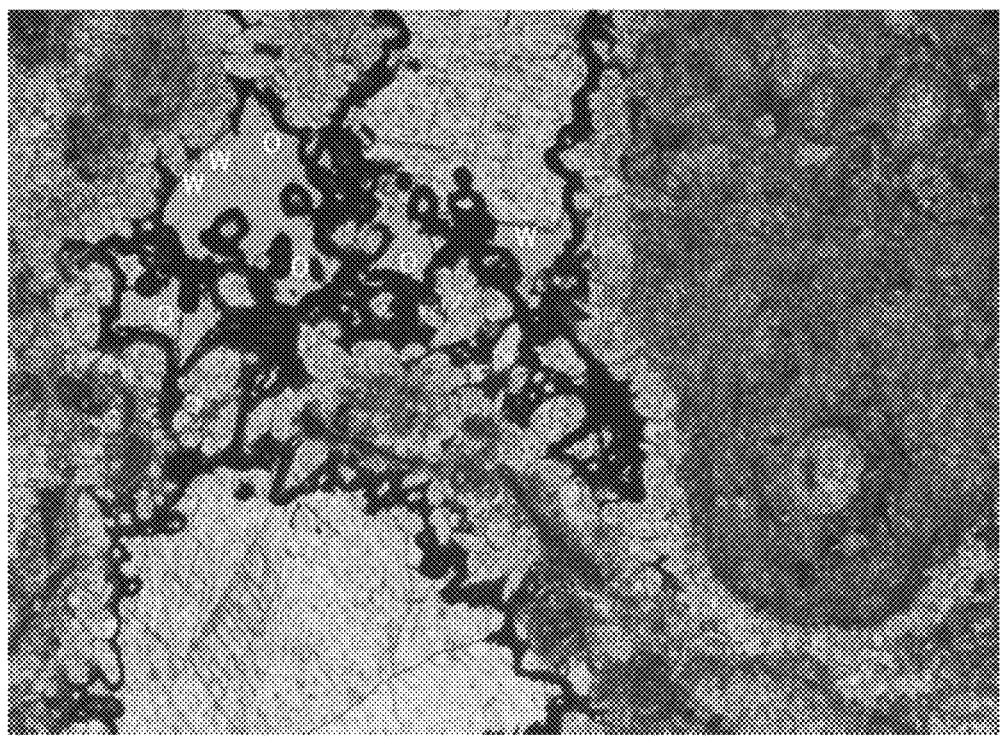
FIG. 2C illustrates an actual exemplary thin image section from a hydrocarbon wet reservoir; W represents interpreted water-wet portions of the pore lining; O represents interpreted oil-wet portions of the pore lining.

FIG. 1C shows an example of a nearly complete hydrocarbon wet reservoir. The rock grains 101 are nearly all wetted by hydrocarbons 105. In addition, there are heavy organic material coatings 109, indicated by gray lines, between hydrocarbons and some parts of rock grains. Coatings with heavy organic material 109, as mentioned above, would be considered hydrocarbon wet. As such, the hydrocarbon wet fraction would be 0.99 whereas the water wet fraction would be 0.01. The wettability indicator would be equal to 0.01. Accordingly, this example would be an example of a highly hydrocarbon wet reservoir sample. FIG. 2C shows an example from an actual thin section obtained from a reservoir.

The above examples only serve to illustrate the various embodiments of the disclosed methods. In practice, reservoir samples may exhibit any range of wettability indicator. In addition, multiple thin sections from a plurality of reservoirs may be analyzed in accordance with the disclosed techniques to obtain wettability indicator values. These wettability indicator values may then be averaged to obtain an average wettability indicator over the entire reservoir.

Figure 4:
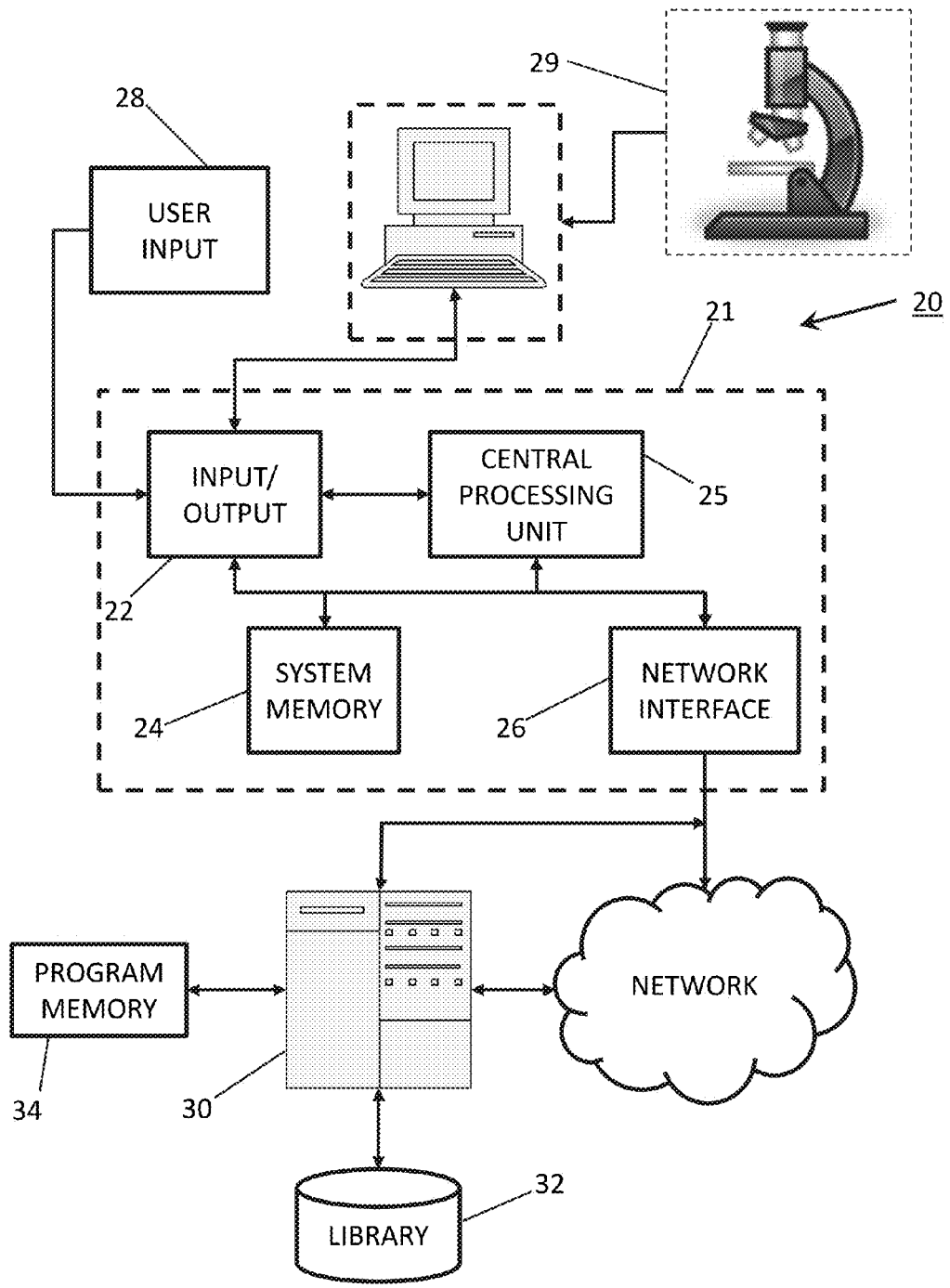
FIG. 4 illustrates a schematic of a system which may be used in conjunction with embodiments of the disclosed methods.

FIG. 4 illustrates, according to an example of an embodiment of a system 20, which may perform the operations described in this specification to perform the operations disclosed in this specification. In this example, system 20 is realized by way of a computer system including an imaging device 29 connected to a workstation 21 which may be connected to a server 30 by way of a network. As mentioned, imaging device 29, although depicted as a microscope, may be any device known those of skill in the art for obtaining digital images of rock samples. Of course, the particular architecture and construction of a computer system useful in connection with this invention can vary widely. For example, system 20 may be realized by a single physical computer, such as a conventional workstation or personal computer, or alternatively by a computer system implemented in a distributed manner over multiple physical computers. Accordingly, the generalized architecture illustrated in FIG. 4 is provided merely by way of example.

As shown in FIG. 4 and as mentioned above, system 20 may include workstation 21, imaging device 29, and server 30. Workstation 21 includes central processing unit 25, coupled to a system bus. Also coupled to a system bus is input/output interface 22, which refers to those interface resources by way of which peripheral functions (e.g., keyboard, mouse, display, etc.) interface with the other constituents of workstation 21. Central processing unit 25 refers to the data processing capability of workstation 21, and as such may be implemented by one or more CPU cores, co-processing circuitry, and the like. The particular construction and capability of central processing unit 25 is selected according to the application needs of workstation 21, such needs including, at a minimum, the carrying out of the functions described in this specification, and also including such other functions as may be executed by a computer system. In the architecture of allocation system 20 according to this example, system memory 24 is coupled to system bus, and provides memory resources of the desired type useful as data memory for storing input data and the results of processing executed by central processing unit 25, as well as program memory for storing the computer instructions to be executed by central processing unit 25 in carrying out those functions. Of course, this memory arrangement is only an example, it being understood that system memory 24 may implement such data memory and program memory in separate physical memory resources, or distributed in whole or in part outside of workstation 21. In addition, as shown in FIG. 4, parameter inputs 28 may be input via input/output function 22, and stored in a memory resource accessible to workstation 21, either locally or via network interface 26.

Network interface 26 of workstation 21 is a conventional interface or adapter by way of which workstation 21 accesses network resources on a network. As shown in FIG. 4, the network resources to which workstation 21 has access via network interface 26 includes server 30, which resides on a local area network, or a wide-area network such as an intranet, a virtual private network, or over the Internet, and which is accessible to workstation 21 by way of one of those network arrangements and by corresponding wired or wireless (or both) communication facilities. In this embodiment of the invention, server 30 is a computer system, of a conventional architecture similar, in a general sense, to that of workstation 21, and as such includes one or more central processing units, system buses, memory resources, network interface functions, and the like. According to this embodiment of the invention, server 30 is coupled to program memory 34, which is a computer-readable medium that stores executable computer program instructions, according to which the operations described in this specification are carried out by allocation system 30. In this embodiment of the invention, these computer program instructions are executed by server 30, for example in the form of a "web-based" application, upon input data communicated from workstation 21, to create output data and results that are communicated to workstation 21 for display or output by peripherals in a form useful to the human user of workstation 21. In addition, library 32 is also available to server 30 (and perhaps workstation 21 over the local area or wide area network), and stores such archival or reference information as may be useful in allocation system 20. Library 32 may reside on another local area network, or alternatively be accessible via the Internet or some other wide area network. It is contemplated that library 32 may also be accessible to other associated computers in the overall network.

The particular memory resource or location at which the measurements, library 32, and program memory 34 physically reside can be implemented in various locations accessible to allocation system 20. For example, these data and program instructions may be stored in local memory resources within workstation 21, within server 30, or in network-accessible memory resources to these functions. In addition, each of these data and program memory resources can itself be distributed among multiple locations. It is contemplated that those skilled in the art will be readily able to implement the storage and retrieval of the applicable measurements, models, and other information useful in connection with this embodiment of the invention, in a suitable manner for each particular application.

According to this embodiment, by way of example, system memory 24 and program memory 34 store computer instructions executable by central processing unit 25 and server 30, respectively, to carry out the disclosed operations described in this specification, for example, by way of which image acquisition, segmentation, image analysis, and measurements of pore linings may be accomplished. These computer instructions may be in the form of one or more executable programs, or in the form of source code or higher-level code from which one or more executable programs are derived, assembled, interpreted or compiled. Any one of a number of computer languages or protocols may be used, depending on the manner in which the desired operations are to be carried out. For example, these computer instructions may be written in a conventional high level language, either as a conventional linear computer program or arranged for execution in an object-oriented manner. These instructions may also be embedded within a higher-level application. Such computer-executable instructions may include programs, routines, objects, components, data structures, and computer software technologies that can be used to perform particular tasks and process abstract data types. It will be appreciated that the scope and underlying principles of the disclosed methods are not limited to any particular computer software technology. For example, an executable web-based application can reside at program memory 34, accessible to server 30 and client computer systems such as workstation 21, receive inputs from the client system in the form of a spreadsheet or images, execute algorithms modules at a web server, and provide output to the client system in some convenient display or printed form. It is contemplated that those skilled in the art having reference to this description will be readily able to realize, without undue experimentation, this embodiment of the invention in a suitable manner for the desired installations. Alternatively, these computer-executable software instructions may be resident elsewhere on the local area network or wide area network, or downloadable from higher-level servers or locations, by way of encoded information on an electromagnetic carrier signal via some network interface or input/output device. The computer-executable software instructions may have originally been stored on a removable or other non-volatile computer-readable storage medium (e.g., a DVD disk, flash memory, or the like), or downloadable as encoded information on an electromagnetic carrier signal, in the form of a software package from which the computer-executable software instructions were installed by allocation system 20 in the conventional manner for software installation.

While the embodiments of the invention have been shown and described, modifications thereof can be made by one skilled in the art without departing from the spirit and teachings of the invention. The embodiments described and the examples provided herein are exemplary only, and are not intended to be limiting. Many variations and modifications of the invention disclosed herein are possible and are within the scope of the invention. Accordingly, the scope of protection is not limited by the description set out above, but is only limited by the claims which follow, that scope including all equivalents of the subject matter of the claims.

The discussion of a reference is not an admission that it is prior art to the present invention, especially any reference that may have a publication date after the priority date of this application. The disclosures of all patents, patent applications, and publications cited herein are hereby incorporated herein by reference in their entirety, to the extent that they provide exemplary, procedural, or other details supplementary to those set forth herein.

What is claimed is:

1. A computer-implemented method of determining wettability in a subsurface reservoir, the method comprising:
    (a) acquiring one or more core samples from the subsurface reservoir;
    (b) preparing a plurality of sections from the core samples for image analysis;
    (c) obtaining a plurality of digital images from each section from a digital imaging device;
    (d) segmenting each digital image into at least a hydrocarbon phase, a water bearing pore phase, and a rock phase; and
    (e) determining a wettability indicator based on a hydrocarbon wet fraction and a water wet fraction, wherein the hydrocarbon wet fraction and the water wet fraction are determined based on the segmenting in (d), and wherein at least (c) through (e) are performed on computer; and
    wherein (e) comprises determining a total pore length, a pore length of hydrocarbon lined pores, and a pore length of unlined pores; and
    wherein the hydrocarbon wet fraction is a fraction of the pore length of hydrocarbon lined pores to the total pore length; and
    wherein the water wet fraction is a fraction of the pore length of unlined pores to the total pore length.

2. The method of claim 1 wherein the pore length of hydrocarbon lined pores comprises a pore length of pores lined with one or more light hydrocarbon materials and one or more heavy organic materials.

3. The method of claim 2 wherein the one or more heavy organic materials comprises bitumen.

4. The method of claim 1 wherein the segmenting comprises edge detection, thresholding, clustering, or combinations thereof.

5. The method of claim 1 wherein the imaging device comprises a confocal laser microscope, a micro-CT, scanning electron microscopy, reflected light microscopy, fluorescent microscopy, or combinations thereof.

6. A system for determining wettability of a subsurface reservoir comprising:
    an imaging device for obtaining one or more digital images of a plurality of imaging sections from one or more core samples from a subsurface reservoir;
    an interface for receiving one or more user inputs;
    a memory resource, the memory resource configured to store the digital images;
    input and output functions for presenting and receiving communication signals to and from a human user;
    one or more central processing units for executing program instructions; and program memory, coupled to the central processing unit, for storing a computer program including program instructions that, when executed by the one or more central processing units, cause the system to perform a plurality of operations for determining wettability of a subsurface reservoir, the plurality of operations comprising:
    (a) segmenting each digital image into at least a hydrocarbon phase, a water bearing pore phase, and a rock phase; and
    (b) determining a wettability indicator based on a hydrocarbon wet fraction and a water wet fraction, wherein the hydrocarbon wet fraction and the water wet fraction are determined based on the segmenting in (a); and
    wherein (b) comprises determining a total pore length, a pore length of hydrocarbon lined pores, and a pore length of unlined pores; and
    wherein the hydrocarbon wet fraction is a fraction of the pore length of hydrocarbon lined pores to the total pore length; and
    wherein the water wet fraction is a fraction of the pore length of unlined pores to the total pore length.

7. The system of claim 6 wherein the pore length of hydrocarbon lined pores comprises a pore length of pores lined with one or more light hydrocarbon materials and one or more heavy organic materials.

8. The system of claim 7 wherein the one or more heavy organic materials comprises bitumen.

9. The system of claim 6 wherein the imaging device comprises a confocal laser microscope, a micro-CT, scanning electron microscopy, reflected light microscopy, fluorescent microscopy, or combinations thereof.

* * * * *